(12) United States Patent
Eid et al.

(10) Patent No.: US 7,960,116 B2
(45) Date of Patent: Jun. 14, 2011

(54) NUCLEIC ACID SEQUENCING METHODS AND SYSTEMS

(75) Inventors: John Eid, San Francisco, CA (US); Alex Dewinter, Albany, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 337 days.

(21) Appl. No.: 12/212,313

(22) Filed: Sep. 17, 2008

(65) Prior Publication Data

US 2009/0087850 A1    Apr. 2, 2009

Related U.S. Application Data

(60) Provisional application No. 60/995,731, filed on Sep. 28, 2007.

(51) Int. Cl.
C12Q 1/68 (2006.01)
C12P 19/34 (2006.01)

(52) U.S. Cl. .......................................... 435/6; 435/91.1

(58) Field of Classification Search .................. None
See application file for complete search history.

(56) References Cited

U.S. PATENT DOCUMENTS

| | | | |
|---|---|---|---|
| 5,001,050 A | 3/1991 | Blanco et al. | |
| 5,198,543 A | 3/1993 | Blanco et al. | |
| 5,405,747 A | 4/1995 | Jett et al. | |
| 5,547,839 A | 8/1996 | Dower et al. | |
| 5,576,204 A | 11/1996 | Blanco et al. | |
| 5,648,245 A | 7/1997 | Fire et al. | |
| 5,674,716 A | 10/1997 | Tabor et al. | |
| 5,674,743 A | 10/1997 | Ulmer | |
| 5,714,320 A | 2/1998 | Kool | |
| 6,210,896 B1 | 4/2001 | Chan | |
| 6,255,083 B1 | 7/2001 | Williams | |
| 6,261,808 B1 | 7/2001 | Auerbach | |
| 6,787,308 B2 | 9/2004 | Balasubramanian | |
| 6,917,726 B2 | 7/2005 | Levene et al. | |
| 7,056,661 B2 | 6/2006 | Korlach et al. | |
| 7,170,050 B2 | 1/2007 | Turner et al. | |
| 7,476,503 B2 | 1/2009 | Turner et al. | |
| 2003/0096253 A1 | 5/2003 | Nelson et al. | |
| 2003/0190647 A1 | 10/2003 | Odera | |
| 2003/0215862 A1 | 11/2003 | Parce et al. | |
| 2004/0048300 A1 | 3/2004 | Sood et al. | |
| 2004/0152119 A1 | 8/2004 | Sood et al. | |
| 2004/0224319 A1 | 11/2004 | Sood et al. | |
| 2004/0259082 A1 | 12/2004 | Williams | |

FOREIGN PATENT DOCUMENTS

| | | |
|---|---|---|
| WO | WO 91/06678 | 5/1991 |
| WO | WO 96/27025 | 9/1996 |
| WO | WO 99/05315 | 2/1999 |

OTHER PUBLICATIONS

Bayley (2006) "Sequencing single molecules of DNA." *Current Opinion in Chemical Biology*, 10: 628-637.
Chan (2005) "Advances in Sequencing Technology" (Review) *Mutation Research*, 573: 1340.
Jett et al. (1989) "High speed DNA Sequencing: An approach based on fluorescent detection of single molecules," *J. Biomol. Struct. Dyn.* 301-309.
Levene et al. (2003) "Zero Mode Waveguides for single Molecule Analysis at High Concentrations," *Science* 299: 682-686.
Werner et al. (2003) "Progress Towards Single Molecule DNA Sequencing: a one color Demonstration," *Journal of Biotechnology*, 102: 1-14.
Eid et al. (2009) "Real-Time DNA Sequencing from Single Polymerase Molecules." *Science*, 323:133-138.

*Primary Examiner* — Young J Kim
(74) *Attorney, Agent, or Firm* — Quine Intellectual Property Law Group, P.C.; Jonathan Alan Quine; Matthew Murphy

(57) ABSTRACT

Sequencing methods that use an exonuclease that comprises template dependent nucleobase binding activity are provided. Related compositions and sequencing systems are also provided.

17 Claims, 4 Drawing Sheets

NUCLEIC ACID SEQUENCING METHODS AND SYSTEMS

CROSS REFERENCE TO RELATED APPLICATIONS

This application claims priority to and benefit of U.S. Ser. No. 60/995,731, filed Sep. 28, 2007, by Eid and Dewinter, entitled "NUCLEIC ACID SEQUENCING METHODS AND SYSTEMS." This prior application is incorporated herein by reference in its entirety for all purposes.

FIELD OF THE INVENTION

This invention is in the field of nucleic acid sequencing, e.g., exonuclease mediated nucleic acid sequencing.

BACKGROUND OF THE INVENTION

Nucleic acid sequencing is ubiquitous to molecular biology and molecular medicine. Goals for sequencing technologies include expanding throughput, lowering reagent and labor costs and improving accuracy. For a relatively recent review of current sequencing technologies, see, e.g., Chan (2005) "Advances in Sequencing Technology" (Review) *Mutation Research* 573: 13-40. A commonly stated goal of current sequencing technology development efforts is to bring the cost for sequencing (or at least resequencing) a genome down to about $1,000. If sequencing costs can be brought down to this level, it will be possible to analyze genetic variation in detail for species and individuals, providing a rational basis for personalized medicine, as well as for identifying relatively subtle causal links between genotypes and phenotypes.

Sequencing methods in use include classical polymerase-mediated enzymatic methods such as Sanger dideoxy sequencing (Sanger et al. (1977) "DNA sequencing with Chain terminating inhibitors," *Proc. Natl. Acad. Sci. USA* 74:5463-5467), capillary based implementations of Sanger sequencing (Swerdlow et al. (1990) "Capillary Gel Electrophoresis for DNA Sequencing laser-induced florescence detection with the Sheath Flow Cuvette," *J. Chromatogr.* 516: 61-67; Cohen et al. (1990) "Separation and Analysis of DNA Sequence Reaction Products by Capillary gel Electrophoresis," *J. Chromatogr.* 49-60; and Dovichi (1997) "DNA Sequencing by Capillary Electrophoresis" *Electrophoresis* 18:2393-2399) and automated implementations of Sanger sequencing (Smith et al. (1986) "Fluorescence detection in automated Sequence Analysis *Nature* 321:674-679; Hood et al. (1987) "Automated DNA Sequencing and Analysis of the Human Genome *Genomics* 1:201-212; Hunkapiller et al. (1991) "Large Scale and Automated DNA Sequence Determination" *Science* 254:59-67). Automated systems are in routine use, such as those from Applied Biosystems (Foster City, Calif.). These commercially available systems include, e.g., 1-Capillary Sequencers, 4-Capillary Sequencers, 16-Capillary Sequencers, 48-Capillary Sequencers and 96-Capillary Sequencers. While this technology is robust, highly developed and accurate, throughput and sequencing costs are still not ideal. State of the art Sanger systems, such as the ABI Prism® 3700 series DNA analyzers, permit sequencing of about 900,000 bp/day at most, with costs still running about $0.001 per base (Chan (2005), infra.). This is still far from the goal of sequencing a genome for $1,000. Sequencing reagent costs per reaction in an automated Sanger system are also likely too high to meet the goal of a $1,000 genome.

Current methods that do not use a polymerase for sequencing, at least partly in an effort to address the cost issues of classical Sanger methods, include sequencing by hybridization (Drmanac R et al. (2002) "Sequencing by hybridization (SBH): advantages, achievements, and opportunities," *Adv Biochem Eng Biotechnol.* 77:75-101; Church (2006) "Genomes for all" *Scientific American.* 294(1):52); direct linear analysis (Chan et. al. (2004) "DNA Mapping Using Microfluidic Stretching and Single Molecule Detection of Fluorescent Site-Specific Tags" *Genome Research* 14: 1137-1146); and nanopore sequencing (Deamer and Branton (2002) "Characterization of Nucleic Acids by Nanopore Analysis," *Acc. Chem. Res.* 35:817-825; Meller et al. (2002) "Single Molecule Measurements of DNA Transported through a Nanopore," *Electrophoresis* 23:2583-2591). Sequencing by hybridization is primarily useful in interrogating whether specific residues occur in a sequence (rather than completely sequencing a nucleic acid de novo, or even completely resequencing a nucleic acid). Direct linear analysis and nanopore sequencing methods are still largely conceptual.

Accordingly, polymerase-based methods are still the most widely applicable sequencing methods. Sequencing approaches that substantially improve throughput over classical Sanger sequencing methods have been developed, including massively parallel pyrosequencing (Leamon et al. (2003) "A massively parallel PicoTiterPlate based platform for discrete picoliter-scale polymerase chain reactions," *Electrophoresis* 24: 682-686), chip-based DNA sequencing by synthesis (DSS) (Seo et al. (2004) "Photocleavable fluorescent nucleotides for DNA on a Chip Constructed by Site-Specific Coupling Chemistry," *Proc. Natl. Acad. Sci. U.S.A.* 101:5488-5493); Sequencing using polymerase colonies (Mitra et al. (2003) "Fluorescent in situ Sequencing on Polymerase Colonies," *Anal. Biochem.* 320: 55-65); and zero mode waveguides (ZMWs) for real-time single molecule sequencing (Levene et al. (2003) "Zero Mode Waveguides for single Molecule Analysis at High Concentrations," *Science* 299:682-686).

Similar to the classical Sanger approaches, these sequencing methods utilize the action of a polymerase to copy a template during sequencing. For example, ZMWs are powerful new sequencing tools that facilitate detection of labeled single nucleotides into single nucleic acids (in real time) as the nucleic acids are copied by a polymerase. Polymerase based "sequencing by incorporation" methods offer advantages inherent in the polymerases being used, such as, e.g., extremely high processivity, extremely low error rates from enzymatic misincorporation and well-characterized reaction enzymology.

One enzymatic sequencing method that is not typically mediated by polymerase activity is "exonuclease sequencing" (reviewed in Chan, 2005, infra, see also Jett et al. (1989) "High speed DNA Sequencing: An approach based on fluorescent detection of single molecules," *J. Biomol. Struct. Dyn.* 301-309). In these methods, a processive exonuclease cleaves labeled nucleotides from a DNA molecule, with the labeled nucleotide being detected and analyzed to provide sequence information (Werner et al. (2003) "Progress Towards Single Molecule DNA Sequencing: a one color Demonstration," *J. Biotechnol.* 102:1-14). Exonuclease-based methods are theoretically promising, because read lengths for this analysis method are potentially very long, with size separation of the cleavage products not being at issue. "Two base" labeling approaches have been proposed in these methods, to overcome problems with multi-labeled nucleic acids (Jett et al. (1995) METHODS FOR RAPID BASE SEQUENCING IN DNA AND RNA WITH TWO BASE LABELING U.S. Pat. No. 5,405,747). Detection of inherent fluorescence of cleaved nucleotides could, potentially, eliminate the need for nucleotide labeling altogether (Ulmer (1997) METHODS AND COMPOSITIONS FOR DNA SEQUENCING U.S. Pat. No. 5,674,743).

Challenges with previous exonuclease-based sequencing methods include poor exonuclease processivity on the highly labeled nucleic acids used in the protocols and incomplete fluorescent label incorporation (Chan, 2005, infra). The present invention overcomes these and other problems.

SUMMARY OF THE INVENTION

The present invention provides enzymatic methods of sequencing a nucleic acid. In the methods, a first strand of a nucleic acid of interest is degraded by an enzyme that displays exonuclease activity (e.g., a polymerase that lacks nucleotide polymerization activity). During degradation, the enzyme transiently matches a nucleobase to a complementary second strand, using standard base-pairing rules. This transient matching is detected, providing an indication of the complementary residue for the complementary strand. The enzyme then releases the nucleobase, degrades a nucleobase from the first strand, and then transiently matches a second base against the second strand. This cycle is repeated, providing a sequence of the nucleic acid of interest.

Accordingly, in a first aspect, a method of sequencing at least a portion of a template nucleic acid is provided. The method includes providing a sequencing reaction mixture. The reaction mixture includes a template nucleic acid strand and a complementary nucleic acid strand that is at least partially complementary to the template nucleic acid strand, when the complementary nucleic acid is hybridized to the template nucleic acid. The mixture also includes at least one labeled nucleobase and an exonuclease that comprises template dependent nucleobase binding activity. A preferred example of such an exonuclease is an intrinsically or extrinsically modified polymerase that comprises exonuclease activity, but that displays low or undetectable nucleotide polymerization activity in the reaction mixture.

The method further includes permitting the sequencing reaction mixture to react, such that the exonuclease transiently binds (or "samples") the labeled nucleobase in a template dependent manner. The exonuclease processively moves along the template as it digests the complementary nucleic acid. Transient binding of the labeled nucleobase by the exonuclease is detected; and, a sequence of the template, or a portion thereof, is determined based upon said detecting.

Any of a variety of approaches can be used to provide the exonuclease activity for the above methods. For example, a polymerase can be used as the exonuclease by either mutating the polymerase to reduce or eliminate polymerase activity, or by altering reaction conditions such that the polymerase displays reduced polymerization activity, while retaining exonuclease activity. For example, the sequencing reaction mixture can include magnesium as the primary cation in the reaction mixture, replacing manganese. This results in a reduction in polymerase activity for many polymerases (e.g., that are attempting to incorporate non native nucleotides), while still permitting the enzyme to function as an exonuclease. In one preferred embodiment, the exonuclease is a DNA polymerase that, in the reaction mixture, is substantially free of polymerase activity, due to extrinsic (e.g., buffer) or to intrinsic (e.g., mutation) modifications. For example, in one embodiment, the polymerase is a φ-29 polymerase that is deficient in polymerase activity in the reaction mixture (e.g., due to a magnesium cation buffer, or due to mutation), and exonuclease competent.

The template and complementary nucleic acids can be produced in any of a variety of ways. These include nicking a duplex DNA (e.g., in which one strand of a duplex DNA is cut with an appropriate nuclease); primer extension of a primer hybridized to a single-stranded nucleic acid; or hybridization (annealing) of complementary nucleic acid strands.

The reaction mixture will generally include at least one labeled nucleobase, and in preferred embodiments can include at least 4 different types of labeled nucleobases (e.g., distinguishably labeled A, C, G, and T or U residues). For example, the reaction mixture optionally includes a plurality of types of nucleobases, each comprising a different distinguishable fluorescent label. For example, the different types of nucleobases can include four different labeled nucleobases, e.g., where each nucleobase is a nucleoside, nucleotide, deoxynucleoside or deoxynucleotide, or analog thereof, and where the labeled nucleobases each comprise an adenine, a guanine, a cytosine, a thymine or a uracil group, or an analog thereof, and where each of the nucleobase types comprises a different distinguishable fluorescent label.

In general, the exonuclease transiently binds a first nucleobase at a first position on the template strand, digests a first nucleobase from the complementary strand, resulting in the exonuclease moving to a second position along the template, where it transiently binds a second nucleobase in a template dependent manner, where each of the transient binding events are detected and where determining the sequence is based on detecting each transient binding event. Thus, the methods can include transiently binding a first nucleobase by the exonuclease in an initial read position along the temple; digesting a nucleobase from the complementary strand; moving the exonuclease to an additional read position along the template; transiently binding a second nucleobase with the exonuclease in the additional read position in a template dependent manner; and, repeating these steps one or more times (and typically many times, to provide long sequence read lengths) with each step comprising digestion of the complementary strand to move the exonuclease into a new additional read position and transient template dependent binding of a nucleobase at the new read position. The steps are repeated for (X) cycles, with (X) being selected by a user, or determined by the length of the complementary strand that can be digested by the exonuclease. Typicaly, (X) is between about 5 and about 50,000 or more. Transient binding of the respective nucleobase at the initial and each additional read position is detected, thereby determining the sequence of the template at each read position along the template.

Most typically, the method includes detecting one or more optical signal generated by transient binding of the nucleobase by the exonuclease. The optical signal can be a fluorescent signal produced by proximity of a fluorophore on the nucleobase to the nucleobase binding site of the enzyme or to the template nucleic acid, and/or, e.g., by cleavage of a fluorophore from the nucleobase by the exonuclease.

The method typically includes assembling sequence information from a plurality of detectable signals produced by binding of a plurality of nucleobases by the exonuclease as the exonuclease travels along the template nucleic acid by digesting the complementary strand, wherein the signals correspond to a nucleobase type and position on the template nucleic acid. Sequence information can also be further assembled based on detection of a plurality of signals from a plurality of reactions collectively comprising overlapping or adjoining template nucleic acids, where the signals in each of the respective reactions are produced by transiently binding a nucleobase to the exonuclease as the exonuclease travels along the template nucleic acid in each respective reaction by digesting the complementary strand in that reaction. The signals correspond to a nucleobase type and position along the template nucleic acid in each of the respective reactions.

The invention also provides sequencing reaction mixtures for practicing the methods. The reaction mixtures can include, e.g., a template nucleic acid, a complementary nucleic acid and an exonuclease that comprises a transient template-dependent nucleobase binding activity, while being substantially free of polymerase activity in the reaction mixture. The reaction can also include one or more labeled nucleobase, buffer constituent, or the like.

In the reaction mixture, the template nucleic acid can include any nucleic acid of interest, e.g., cloned, amplified or genomic DNA. The template nucleic acid and complementary nucleic acid can be hybridized together, or can be separate in the reaction mixture (e.g., where the strands are annealed together prior to sequencing). The template nucleic acid can be hybridized to one or more complementary nucleic acids. As noted in the methods, the complementary nucleic acids can be produced by nicking a complementary nucleic acid hybridized to the template nucleic acid, or the complementary nucleic acid can be a primer or a primer extension product.

The exonuclease can be a polymerase that displays low polymerization activity in the reaction mixture, e.g., where the polymerase is a φ-29 polymerase and the reaction mixture comprises magnesium as the primary cation in the mixture. Similarly, the polymerase can be a mutant polymerase that displays low polymerization activity. Examples of appropriate polymerases include class A, class B, class C, class D, class X, class Y or class RT polymerases that are deficient in polymerase activity in the reaction mixture, due to reaction conditions, and/or due to a mutation as compared to a wild type form of the polymerase. For example, the mutant polymerase can be a mutant of a class A, class B, class C, class D, class X, class Y or class RT polymerase that is deficient in polymerase activity in the reaction mixture as compared to a wild type form of the polymerase and that also displays enhanced exonuclease activity as compared to said wild type polymerase. This enhancement can take the form of improved processivity, improved labeled nucleobase retention time, or the like.

As noted, the labeled nucleobase typically comprises a fluorescent label. The reaction mixture can include four different labeled nucleobases, where each nucleobase is a nucleoside, nucleotide, deoxynucleoside or deoxynucleotide, or analog thereof, and wherein the labeled nucleobases each comprise an adenine, guanine, cytosine, thymine or uracil group, or analog thereof. Optionally, each of the nucleobase types comprises a different distinguishable fluorescent label. In one preferred embodiment, the nucleobases can include at least one analogue of a nucleotide that comprises a labeled phosphate group, though a variety of other labeling strategies are also appropriate. The reaction mixture may include a single template molecule for analysis, e.g., in single molecule sequencing applications.

In a related aspect, the invention provides a sequencing system. The system includes a reaction chamber and a detector configured to detect a signal from the reaction chamber. The signal in the system results from a transient template-dependent binding of a labeled nucleobase by a polymerization activity deficient exonuclease in the reaction chamber. A sequence assembly module assembles template nucleic acid sequence information based upon detection of the signal.

Optionally, the system includes a reaction mixture as noted above, e.g., where the reaction chamber contains a sequencing reaction mixture that includes a template nucleic acid, a complementary nucleic acid, an exonuclease that comprises a transient template-dependent nucleobase binding activity, which exonuclease is substantially free of polymerase activity in the reaction mixture, and, a labeled nucleobase.

In one preferred embodiment, the system is configured for single molecule sequencing. For example, the reaction chamber can comprise a zero mode waveguide, configured for detection of single molecule sequencing reactions.

Most typically, the detector detects an optical signal, e.g., the detector is typically configured to detect one or more fluorescent or luminescent signal(s).

The analysis module optionally assembles nucleic acid sequence based upon detection of a plurality of signals from the reaction chamber. The signals are typically correlated to template nucleotides based upon the signal type and timing of the signals.

Kits for practicing the invention are also provided. Such kits can include, e.g., the reaction mixture, or components thereof, e.g., in combination with instructions for practicing the methods herein and appropriate packaging and containers. Components designed to function with the system are also a feature of the invention, including arrays of reaction mixtures, zero-mode waveguides configured for practicing the methods of the invention (e.g., by binding an exonuclease to the walls of ZMWs) and the like.

DETAILED DESCRIPTION

Figure 1:
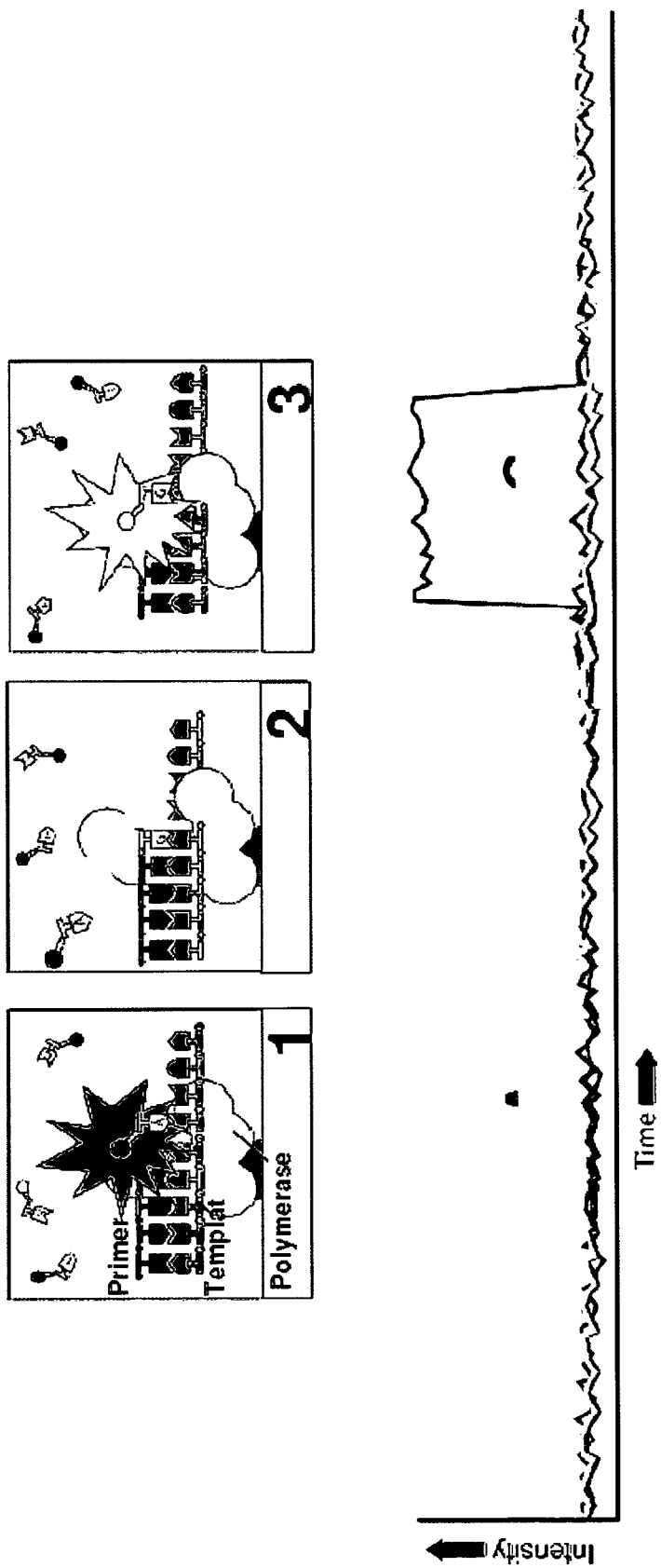
FIG. 1 provides a schematic illustration of a sequencing reaction of the invention, and a schematic histogram of signal output from the reaction.

The present invention provides new enzymatically mediated methods of sequencing nucleic acids, as well as compositions, kits and systems useful in practicing the methods. The methods utilize a processive enzyme that comprises exonuclease activity and that also comprises transient nucleobase binding activity, in which the enzyme transiently matches the nucleobase against a template strand using standard base-pairing rules. The enzyme moves along the template strand by digesting a complementary strand hybridized to the template strand, transiently matching nucleobases against the template strand as it digests the complementary strand. Each transient matching is detected, typically by detecting the transient matching of a labeled nucleobase.

This process has a number of significant advantages over existing sequencing technologies. For example, the read length of the technology is not limited by the ability to size separate a sequencing product, as is the case for standard Sanger sequencing methods. Further, the nucleobase does not have to be consumed by the transient matching process (although, in some optional embodiments, the enzyme also cleaves the label from the nucleobase, in which case the process does consume the labeled nucleobase). This reduces reagent costs for the process. In addition, incorporation of labeled analogues into a sequencing product is not required, potentially broadening the types of labels and nucleobases that can be used, as the relevant nucleobase does not have to be compatible with incorporation into a nucleic acid by a polymerase. Similarly, labeled nucleotides do not have to be incorporated into a template to be sequenced, as is the case for previous exonuclease sequencing protocols, which rely on release of a labeled nucleotide from the sequencing template. Further, because the methods are amenable to single-molecule sequencing protocols, cloning of template nucleic acids is generally not necessary, greatly increasing the throughput of the method as compared to standard Sanger methods, which typically do require cloning of template nucleic acids. Finally, the enzyme with exonuclease activity does not have to be strand displacing, increasing the types of enzymes that can be adapted for the methods. These and other advantages are described in detail herein.

Further Details Regarding the Sequencing Method

The present invention provides new methods for sequencing nucleic acids. In the methods, a nucleic acid of interest is sequenced using an enzyme having exonuclease activity and nucleotide "sampling" activity. For example, a polymerization-defective polymerase with exonuclease activity can be used, by monitoring which nucleotide or other nucleobase that the enzyme transiently binds ("samples") as it digests a complementary strand hybridized to a template strand of the nucleic acid of interest. Thus, the sampling process involves transiently binding a labeled nucleobase that is complementary to a base in the template strand at the sampling site (that is, the labeled nucleobase is the correct base to specifically pair with the base in the template strand, according to typical base-pairing rules). The enzyme, substantially lacking polymerization activity, does not incorporate the base into the complementary strand, but, rather, releases it after this sampling event. Nucleobase sampling is detected by monitoring transient binding of the labeled nucleobase at the sampling site. In preferred aspects, this method is applicable to single-molecule sequencing, in that individual sampling events by the enzyme are detected in real time as the enzyme samples the nucleobase at the sampling site.

A nucleic acid of interest can be provided from essentially any source, including genomic DNA, amplified DNA or RNA, cloned DNA or RNA, cDNA, RNA, mRNA or the like. During sequencing, the nucleic acid of interest is typically at least partly double stranded. Because the enzyme transiently samples a nucleobase by matching it to a site on the template strand of the nucleic acid of interest, the nucleic acid of interest will typically be single stranded at the sampling or "read" site. Further, because the enzyme moves processively along the template strand by digesting the complementary nucleic acid that is hybridized to the template strand, the nucleic acid of interest is double stranded for at least an initial distance along the template strand, downstream from the sampling site.

The enzyme samples a labeled nucleobase at the sampling site, resulting in a signal being generated by the label during sampling. For example, the enzyme can be an exonuclease such as a polymerase enzyme that lacks polymerization activity, where the polymerase matches the nucleobase against the template strand (following typical base-pairing rules) at the sampling position (base N), e.g., located at the end of the complementary strand proximal to the sampling site. This sampling by the enzyme of the labeled nucleobase results in a detectable signal that provides an indication of which base is sampled, and, thus, which base is present at the N position of the template strand. As the exonuclease digests the complementary strand, the enzyme moves to the N−1 position along the template relative to the initial sampling position, and the enzyme samples a labeled nucleobase at the N−1 position, resulting in a detectable signal that identifies which nucleobase is sampled at the N−1 position, and, thus, the identity of the N−1 position for the template strand. The enzyme continues through repeated cycles of sampling and exonuclease digestion through the N−2 ... N−X positions, until the end of the template nucleic acid is reached, or until the enzyme degrades or otherwise looses activity. Typically, e.g., where the relevant enzyme is a polymerization deficient polymerase that comprises 5' exonuclease activity, the reaction proceeds in a 5'-3' direction. However, the method is not limited to any particular directionality of exonuclease digestion, as exonuclease enzymes that can hydrolyse phosphodiester bonds from either the 3' or 5' terminus of a polynucleotide molecule are known and available. In any case, the signal information from each of the sampling (or "read") positions along the template provides the sequence of the template (and, by standard base-pairing rules, the sequence of the complementary nucleic acid).

Schematic Illustration of the Method

FIG. 1 provides an example schematic illustration of methods of the invention. As show, steps in exonuclease mediated sequencing of the invention include: 1) sampling by the polymerase or other enzyme, at the 3' position of the primer, of a labeled nucleoside; 2) clipping off of the next base on the primer with the exonuclease activity of the enzyme, and 3) sampling the resulting new 3' position by the enzyme with a labeled nucleoside. A resulting schematic trace of signal intensity resulting from the sampling events in the systems of the invention is shown against time below the schematic depictions of the overall process.

Figure 2:
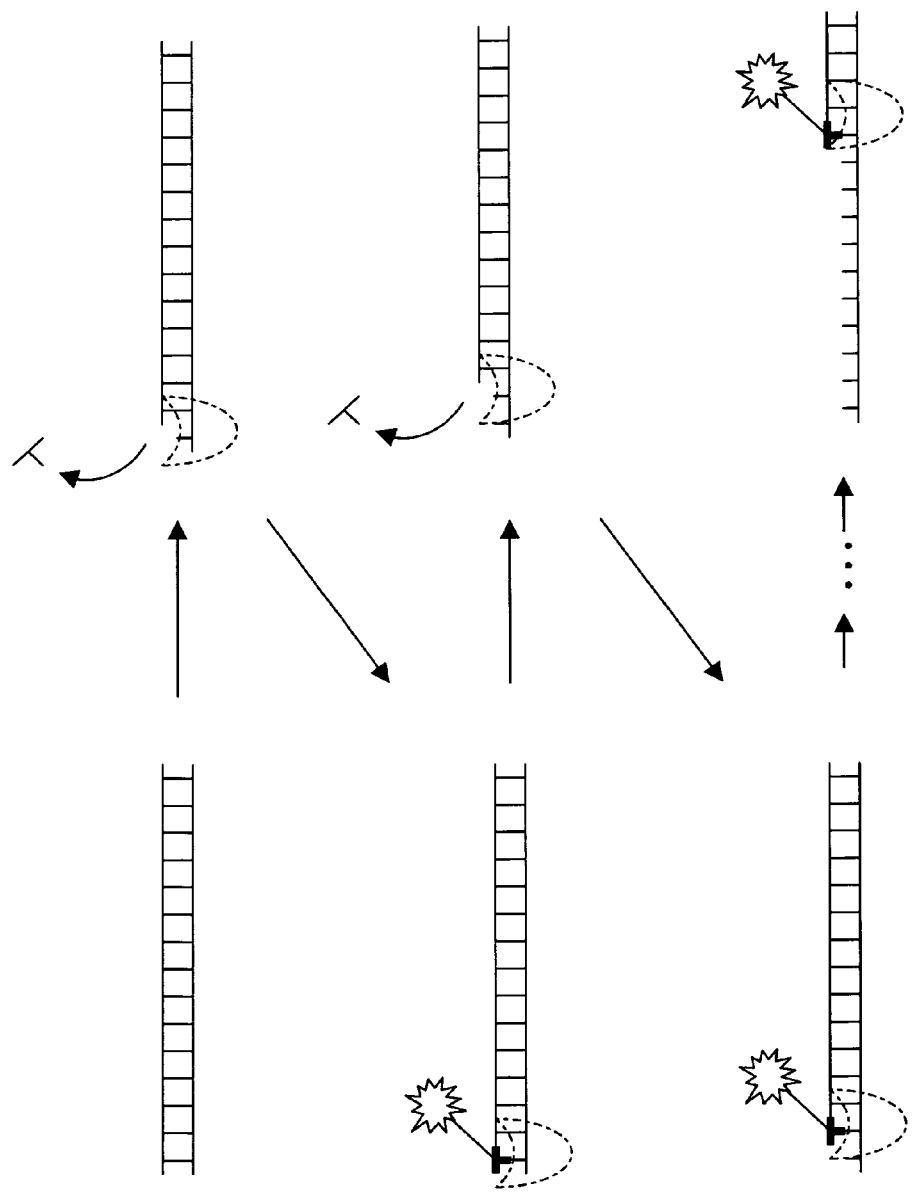
FIG. 2 provides a schematic illustration of a sequencing reaction of the invention showing cycles of nuclease activity, nucleobase binding and release and further nuclease activity.

This process is further schematically illustrated in FIG. 2. As shown in the top panel, the exonuclease cleaves the complementary strand to the template, exposing a site for nucleobase binding. As shown in the middle panel, the nucleobase binds the site in a template strand specific manner, resulting in a signal event (e.g., a photon emission). The nucleobase is then released from the site in a form that does not produce the signal. As shown in the bottom panel, the exonuclease then cleaves the next nucleotide from the complementary strand, and the process is repeated.

Enzymes

The enzyme to be used in the methods of the invention comprises exonuclease activity and nucleobase sampling activity, as noted herein. At least two different approaches can be used to provide enzymes that have this activity. First, buffer/sequencing reaction conditions can be modulated to provide this activity from existing enzymes. For example, by switching the cation in a typical polymerase sequencing buffer from manganese to magnesium, a polymerase will substantially loose its polymerization activity, while retaining sampling and exonuclease activities of the enzyme. Second, the enzyme of the invention can be produced by modification of existing enzymes that comprise exonuclease activity, such as by mutation of existing polymerases or exonucleases.

For example, with respect to the first "extrinisic modification" approach, a polymerase enzyme such as a φ-29 polymerase (or other protein primed polymerases) can be used in the sequencing reaction, in a buffer that is depleted in manganese, but that comprises magnesium. For nomenclature on this family of enzymes, see also, Meijer et al. (2001) "Φ29 Family of Phages" *Microbiology and Molecular Biology Reviews*, 65(2):261-287. For a description of general mechanisms of action for protein primed polymerases, see Mendez et al. (1997) "Protein-primed DNA replication: a transition between two modes of priming by a unique DNA polymerase," *EMBO J.* 16(9): 2519-2527. Examples of appropriate DNA polymerases that can be rendered in active with respect to polymerization include Φ29 and other protein primed polymerases, B103, GA-1, PZA, Φ15, BS32, M2Y, Nf, G1, Cp-1, PRD1, PZE, SF5, Cp-5, Cp-7, PR4, PR5, PR722, or L17, or the like.

Polymerase enzymes can also be "intrinsically modified" such that the enzymes have nucleotide sampling and exonuclease activity, but are not polymerization competent. Polymerases provide good starting points to produce enzymes of the invention, because they have nucleotide sampling and exonuclease activity and because the active sites for virtually all polymerases are known or can be inferred by comparison to well characterized homologs. Polymerases can be modified by mutation (or, alternately, chemical modification) to reduce or eliminate polymerization activity. Thus, in the context of the invention, a "polymerase" can partially or completely lack polymerization activity; that is, a polymerase enzyme of the invention can be termed a "polymerase" based simply upon homology to a wild-type polymerase that does comprise polymerization activity under appropriate polymerization conditions. For example, an intrinsically modified polymerase of the invention (e.g., that includes exonuclease activity and sampling activity, but has reduced or eliminated polymerization activity) can be derived by mutation from a polymerase that comprises nucleic acid polymerization activity. Polymerases that lack polymerization activity, but that, e.g., retain nucleotide sampling and exonuclease activity can also be termed "polymerization-defective polymerases," or, where nucleotide sampling and exonuclease functions are preserved, can be termed "exonuclease-competent, nucleotide sampling-competent, polymerization-defective polymerases."

Polymerases provide preferred enzymes that can be adapted, intrinsically or extrinsically, to provide an exonuclease with nucleobase sampling activity. In this context, an exonuclease of the invention comprises exonuclease activity (the ability to degrade or remove nucleotides from an end of a nucleic acid polymer); in the context of many of the methods herein, such enzymes also preferably include nucleotide sampling activity. A wide variety of polymerases (including those already noted) are known, having been the subject of decades of focused research, and as a result of their role as basic research and diagnostic tools in molecular biology and molecular medicine. DNA template-dependent DNA polymerases have been classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y). For a review of recent nomenclature, see, e.g., Burgers et al. (2001) "Eukaryotic DNA polymerases: proposal for a revised nomenclature" J Biol Chem. 276(47):43487-90. For a review of polymerases generally, see, e.g., Hübscher et al. (2002) EUKARYOTIC DNA POLYMERASES Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398.

The basic mechanisms of action for many polymerases have been determined. The sequences of literally hundreds of polymerases are publicly available, and the crystal structures for many of these have been determined, or can be inferred based upon similarity to solved crystal structures for homologous polymerases. Furthermore, a variety of polymerases adapted to single molecule sequencing reactions are known, including mutant forms that display the ability to incorporate labeled nucleotides (see, e.g., Hanzel et al. POLYMERASES FOR NUCLEOTIDE ANALOGUE INCORPORATION, WO 2007/076057), and polymerases that are active when bound to surfaces (useful in single molecule sequencing reactions in which the enzyme is fixed to a surface, e.g., conducted in a zero mode waveguide; see Hanzel et al. ACTIVE SURFACE COUPLED POLYMERASES, WO 2007/075987 and Hanzel et al. Protein Engineering Strategies to Optimize Activity of Surface ATTACHED PROTEINS, WO 2007/075873). Similarly, available modified polymerases that can incorporate labeled nucleotides can provide the enzymes of the invention, after intrinsic or extrinsic modification. For example, DNA polymerase mutants have been identified that have improved nucleotide analogue binding relative to wild-type counterpart enzymes. For example, Vent$^{A488L}$ DNA polymerase can incorporate (and, thus, sample) certain non-standard nucleotides with a higher efficiency than native Vent DNA polymerase. See Gardner et al. (2004) "Comparative Kinetics of Nucleotide Analog Incorporation by Vent DNA Polymerase" *J. Biol. Chem.*, 279(12), 11834-11842; Gardner and Jack "Determinants of nucleotide sugar recognition in an archaeon DNA polymerase" *Nucleic Acids Research,* 27(12) 2545-2553.

Other enzymes that comprise sampling activity such as reverse transcriptases, RNA polymerases and the like can also serve as starting points for enzymes with sampling activity. Where these enzymes lack exonuclease activity, this activity can be added by genetically or chemically fusing the active/sampling site for the enzyme to an exonuclease domain, e.g., derived from a polymerase or another exonuclease. Appropriate exonucleases (which can found as individual enzymes, or as parts of larger enzyme complexes) cleave nucleotides one at a time from an end of a polynucleotide chain. These enzymes can hydrolyse phosphodiester bonds from either the 3' or 5' terminus of a polynucleotide molecule. Example available exonucleases include Exonuclease I, e.g., from *E. coli*, Exonuclease III, e.g., from *E. coli*, Exonuclease VII, Lambda Exonuclease, RecBCD Nuclease, *E. coli* Rec J Exonuclease, T5 Exonuclease (all commercially available, e.g., from EPICENTRE Biotechnologies (Madison, Wis.).

Modification of existing enzymes to reduce or eliminate polymerization activity while retaining sampling and nuclease activity can be performed using mutation/selection protocols designed to select for the appropriate activities. For example, the active polymerization site of a polymerase can be randomly mutated by any available mutation procedure to produce polymerases with desired activities. Desired activity includes reduced polymerization, improved exonuclease processivity, improved (e.g., longer) sampling or "latency" times for the nucleobase during sampling, improved sampling specificity, ability to sample the labeled nucleobase of interest, and the like. In general, any available mutagenesis procedure can be used for making such mutants. Such mutagenesis procedures optionally include selection of mutant enzymes for one or more activity of interest. Procedures that can be used include, but are not limited to: site-directed point mutagenesis, random point mutagenesis, in vitro or in vivo homologous recombination (DNA shuffling), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill.

Optionally, mutagenesis can be guided by known information regarding the active site or mechanism of action for an available enzyme, or of a known variant (e.g., using an existing mutant polymerase that already displays one or more desirable property, such as those WO 2007/076057, WO 2007/075987 or WO 2007/075873). Such known information can include e.g., sequence, sequence comparisons, physical properties, crystal structure and/or the like as discussed above. However, in another class of embodiments, modification can be essentially random (e.g., as in classical DNA shuffling). Modification will often be a combination of designed and random, e.g., by randomly shuffling or mutating the active site, while leaving the rest of the enzyme constant.

Selection procedures are conducted based on the property to be selected for. More than one selection scheme can, and often will, be applied to a library of mutants to identify those that have properties of interest. For example, after shuffling or other mutagenesis procedures to generate a library of mutants of the relevant enzyme, the library can first be "positively" selected to identify members with sampling or exonuclease activity and then can be "negatively" selected to eliminate those members that comprise polymerase activity (or these screens can be run in reverse, eliminating polymerization competent mutants and then identifying those with exonuclease or polymerization activity). Screens can be done using available methods.

For example, strains of E. coli and other cells exist that are polymerase deficient under certain environmental conditions (e.g., at certain temperatures). Library members can be selected against by identifying those members that are rescued by transforming the library member into the cell. Similarly, library members can be put under the control of a strong promoter, and tested for elevated polymerization activity, using a polymerization dependent reporter, or by testing for DNA copying mediated by the library member (in vitro or in vivo). For example, a lethal protein such as Barnase can be expressed at minimal non-lethal levels from an plasmid-based expression cassette; over copying of the plasmid in a system that requires activity of the library member will lead to leathality, and selection against members that comprise polymerization activity. Exonuclease activity can be selected for by monitoring exonuclease digestion, e.g., by monitoring the formation of digestion products mediated by the relevant library member, or by monitoring an effect on a reporter. For example, over expression of an exonuclease can be used to inhibit expression of a lethal reporter such as barnase, or to inhibit expression of an optical or other reporter such as LacZ. For example, overexpression of the exonuclease can degrade a plasmid carrying the reporter, inhibiting expression of the reporter. This effect can be enhanced by nicking the plasmid, e.g., by co-expressing an endonuclease that is specific for one or more sites on the reporter plasmid (or by expressing an essentially random nicking enzyme such as DNase I). Nicking and/or endonuclease and/or reporter expression can be inducible, using standard inducible promoters.

In another example, a fluorescence based assay can be used. For example, In a manner similar to molecular beacon technology, the donor and quencher can be placed on a hairpin such that when the hairpin is in a "closed" conformation, signal from the donor is quenched. When the exonuclease activity digests one end of the hairpin far enough to release the hairpin, the fluorescence signal turns "on". This results in a detectable signal, which can be used for selection. In another embodiment, the exonuclease can be allowed to digest an initially double stranded template, with an intercalating dye being used to quantify the presence of remaining double stranded DNA. This can be done at different time points to yield kinetic information. See also, Chembiochem. 2007 8(4): 395-401.

Screening can also be performed using the end-use sequencing system application itself. For example, high-throughput single molecule sequencing reactions can be run on known nucleic acids. Clones that produce enzymes that accurately sequence the known nucleic acid, where the data corresponds to exonuclease digestion and sampling, are selected in the screen. For example, ZMWs can be used for high throughput real-time single molecule sequencing (e.g., Levene et al. (2003) "Zero Mode Waveguides for single Molecule Analysis at High Concentrations," Science 299:682-686; U.S. Pat. Nos. 7,033,764, 7,052,847, 7,056,661, and 7,056,676, the full disclosures of which are incorporated herein by reference in their entirety for all purposes.). If the methods of the invention are performed using ZMWs or other high-throughput optical confinement apparatus, observation of the sequencing reaction can be used as the selection screen to identify library members with desirable properties.

Screening in the end use application (e.g., using the sequencing methods and systems herein) is desirable where features that are most easily detectable in the sequencing system at issue are to be screened for. For example, if increased residence time of labeled nucleotides are selected for, it is desirable to screen for this property using a sequencing system of the invention, as the most straightforward way to screen for increased residence time is simply to observe residence times. This is often the case for kinetic parameters of interest, such as binding specificity of a nucleobase by a recombinant enzyme, rate of nucleobase release by the recombinant enzyme, or branching rate of the recombinant enzyme (the "branching rate" is the rate of dissociation of a nucleotide or nucleotide analogue from the polymerase active site without incorporation of the nucleotide or nucleotide analogue, where the nucleotide or nucleotide analogue if it were incorporated would correctly base-pair with a complementary nucleotide or nucleotide analogue in the template). For a more thorough discussion of enzyme kinetics, see, e.g., Berg, Tymoczko, and Stryer (2002) Biochemistry, Fifth Edition, W. H. Freeman; Creighton (1984) Proteins: Structures and Molecular Principles, W. H. Freeman; and Fersht (1985) Enzyme Structure and Mechanism, Second Edition, W. H. Freeman. For an extended discussion of polymerase enzyme kinetics, including a description of a 2-D matrix to describe possible kinetic states of a polymerase-template-dNTP system, see also, Hanzel et al. POLYMERASES FOR NUCLEOTIDE ANALOGUE INCORPORATION, WO 2007/076057. Essentially any kinetic feature of interest can be selected for (or against) in a sequencing system of the invention, by identifying those library members that display the desired (or undesired) property during sequencing according to the present invention.

Figure 3:
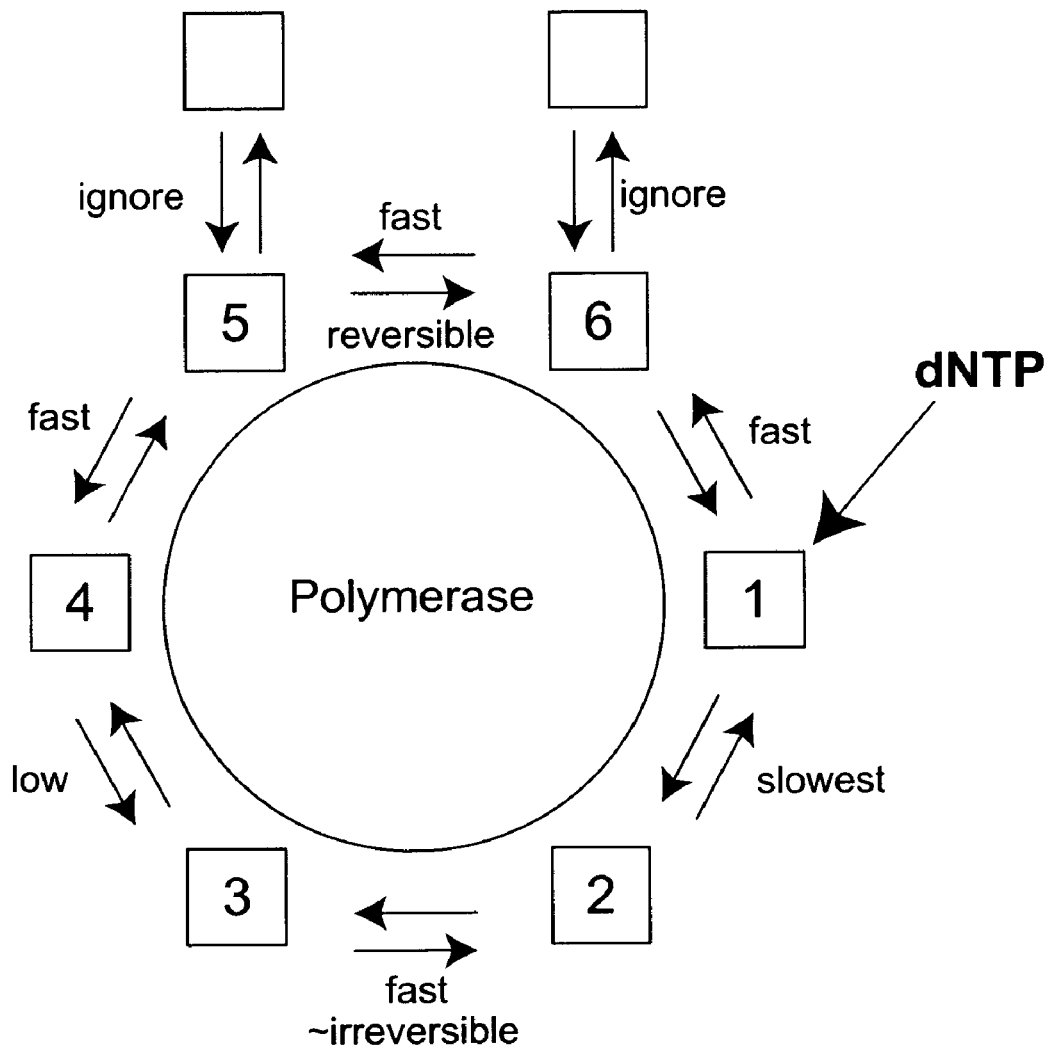
FIG. 3 provides a schematic illustration of polymerase kinetics.

For example, FIG. 3 provides a 2-D matrix that models possible kinetic states of a polymerase-template-dNTP system (for more details on such kinetic models, see also, WO 2007/076057). In exonuclease embodiments that use intrinsically or extrinsically modified polymerases, the catalysis step is inhibited, which can be done, e.g., by inhibiting this step directly, or by inhibiting a conformational step leading to catalysis. PPi release is unnecessary in the exonuclease mediated approach, as no chemical bond needs to be broken for nucleobase immobilization to occur. Selection strategies as noted herein can be used to select for modified activity at any point in the kinetic pathway.

Additional information on mutation and selection formats is found in: Sambrook et al., *Molecular Cloning—A Laboratory Manual*(3rd Ed.), Vol. 1-3, Cold Spring Harbor Laboratory, Cold Spring Harbor, N.Y., 2000 ("Sambrook"); *Current Protocols in Molecular Biology*, F. M. Ausubel et al., eds., Current Protocols, a joint venture between Greene Publishing Associates, Inc. and John Wiley & Sons, Inc., (supplemented through 2006) ("Ausubel")) and *PCR Protocols A Guide to Methods and Applications* (Innis et al. eds) Academic Press Inc. San Diego, Calif. (1990) (Innis). The following publications and references cited within provide still additional detail on mutation formats: Arnold, *Protein engineering for unusual environments, Current Opinion in Biotechnology* 4:450-455 (1993); Bass et al., *Mutant Trp repressors with new DNA-binding specificities, Science* 242:240-245 (1988); Botstein & Shortle, *Strategies and applications of in vitro mutagenesis, Science* 229:1193-1201 (1985); Carter et al., *Improved oligonucleotide site-directed mutagenesis using M13 vectors, Nucl. Acids Res.* 13: 4431-4443 (1985); Carter, *Site-directed mutagenesis, Biochem. J.* 237:1-7 (1986); Carter, *Improved oligonucleotide-directed mutagenesis using M13 vectors, Methods in Enzymol.* 154: 382-403 (1987); Dale et al., *Oligonucleotide-directed random mutagenesis using the phosphorothioate method, Methods Mol. Biol.* 57:369-374 (1996); Eghtedarzadeh & Henikoff, *Use of oligonucleotides to generate large deletions, Nucl. Acids Res.* 14: 5115 (1986); Fritz et al., *Oligonucleotide-directed construction of mutations: a gapped duplex DNA procedure without enzymatic reactions in vitro, Nucl. Acids Res.* 16: 6987-6999 (1988); Grundström et al., *Oligonucleotide-directed mutagenesis by microscale 'shot-gun' gene synthesis, Nucl. Acids Res.* 13: 3305-3316 (1985); Kunkel, *The efficiency of oligonucleotide directed mutagenesis*, in *Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Point Mismatch Repair, Cell* 38:879-887 (1984); Kramer et al., *Improved enzymatic in vitro reactions in the gapped duplex DNA approach to oligonucleotide-directed construction of mutations, Nucl. Acids Res.* 16: 7207 (1988); Ling et al., *Approaches to DNA mutagenesis: an overview, Anal Biochem.* 254(2): 157-178 (1997); Lorimer and Pastan *Nucleic Acids Res.* 23, 3067-8 (1995); Mandecki, *Oligonucleotide-directed double-strand break repair in plasmids of Escherichia coli: a method for site-specific mutagenesis, Proc. Natl. Acad. Sci. USA*, 83:7177-7181 (1986); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Nambiar et al., *Total synthesis and cloning of a gene coding for the ribonuclease S protein, Science* 223: 1299-1301 (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Sieber, et al., *Nature Biotechnology,* 19:456-460 (2001); Smith, *In vitro mutagenesis, Ann. Rev. Genet.* 19:423-462 (1985); *Methods in Enzymol.* 100: 468-500 (1983); *Methods in Enzymol.* 154: 329-350 (1987); Stemmer, *Nature* 370, 389-91 (1994); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Wells et al., *Importance of hydrogen-bond formation in stabilizing the transition state of subtilisin, Phil. Trans. R. Soc. Lond.* A 317: 415-423 (1986); Wells et al., *Cassette mutagenesis: an efficient method for generation of multiple mutations at defined sites, Gene* 34:315-323 (1985); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors, Methods in Enzymol.* 100:468-500 (1983); and Zoller & Smith, *Oligonucleotide-directed mutagenesis: a simple method using two oligonucleotide primers and a single-stranded DNA template, Methods in Enzymol.* 154:329-350 (1987). Additional details on many of the above methods can be found in *Methods in Enzymology* Volume 154, which also describes useful controls for trouble-shooting problems with various mutagenesis methods.

The recombinant enzyme is optionally engineered to include additional features exogenous or heterologous to a corresponding wild-type enzyme. For example, the recombinant enzyme optionally includes one or more exogenous affinity tags, e.g., purification or substrate binding tags, such as a 6 His tag sequence, a GST tag, an HA tag sequence, a plurality of 6 His tag sequences, a plurality of GST tags, a plurality of HA tag sequences, a SNAP-tag, or the like. These may be inserted into any of a variety of positions within the protein, and are preferably at one or more termini e.g., C terminus or N terminus of the protein, and are more preferably, at a region that is most distal to the active site(s) in the 3D structure of the protein. The inclusion of such tags facilitates purification and handling of the enzyme during sequencing, e.g., where it is advantageous to fix the enzyme in a particular location during the sequencing reaction. This can be useful to fix or orient the enzyme such that signals generated by it are more uniformly read by detection apparatus, to normalize activity of the enzyme by holding it in a particular orientation, to provide for reagent washing across the fixed enzyme, or the like. Additional details regarding surface binding of enzymes for these and other purposes is found in WO 2007/076057, WO 2007/075987 and WO 2007/075873.

Nucleobases and Labeling Strategies

A nucleobase of the invention can be any moiety that specifically hybridizes with a nucleotide reside of the template strand at the read site. Most typically, the nucleobase will be a nucleotide (e.g., an A, G, C, T, or U) or a nucleotide analog such as a labeled form of such a nucleotide. However, because the nucleotide does not need to be (and preferably is not) incorporated, the relevant moiety does not necessarily require a phosphate group, or other structural elements that permit nucleotide incorporation by a polymerase. Thus, the nucleobase can be a nucleoside or nucleoside analog, or even a peptide nucleic acid residue or other chemical moiety, so long as the nucleobase can be sampled by the polymerase and as long as the residue is specific for the template-strand nucleotide residue at the read site. As discussed above, mutation strategies can be used to produce enzymes that have desired properties; such properties can include the ability to sample non-standard nucleotides.

Accordingly, the nucleobase can be a nucleoside, a nucleotide, deoxynucleoside or deoxynucleotide, or analog thereof. The nucleobases can individually comprise an adenine, guanine, cytosine, thymine or uracil group, or analog thereof. Optionally, each of the nucleobase types can include a distinguishable label, such as a fluorophore. Examples of labeled nucleobases include those that include fluorophore and/or dye moieties. For example, the nucleobase can be a labeled nucleotide, e.g., a base, sugar and/or phosphate labeled nucleotide or analog. A wide variety of labeled nucleobases are known; see, e.g., *The Handbook—A Guide to Fluorescent Probes and Labeling Technologies, Tenth Edition* (2005) (available from Invitrogen, Inc./Molecular Probes). Fluorescent labels, luminescent labels, quantum dots, and the like are all appropriate labels for the sequencing methods and compositions herein.

For example, a variety of labels are cleaved by action of the enzyme, e.g., phosphate labels are cleaved from the nucleobase analogue as it is sampled (typically providing a signal upon release of the label). One example class of nucleotide analogues are phosphate-labeled nucleotide analogues, including mono-deoxy phosphate-labeled nucleotide analogues and/or dideoxy phosphate-labeled nucleotide analogues. For example, the nucleotide analogue can be a labeled nucleotide analogue having more than 3 phosphate groups (e.g., where the nucleotide analogue is a triphosphate, a tetraphosphate, a pentaphosphate a hexaphosphate, a heptaphosphate, etc.). See also, WO 2007/076057.

In one class of embodiments, labels are not cleaved by the enzyme from the nucleobase. Typically, for these embodiments, proximity to the sampling site results in a signal, rather than dye cleavage. This can be accomplished, e.g., by labeling the nucleobase with one member of a fluorescence resonance energy transfer (FRET) dye pair, and labeling the sampling site of the enzyme with the other member. Other detectable non-FRET dye interactions can be used in an essentially similar manner. A variety of FRET and other dye pairs are readily available. Any of a variety of different label moieties are incorporated into nucleotide analogs using available methods (and many such labeled analogs are also commercially available). Such groups can include fluorescein labels, rhodamine labels, cyanine labels (e.g., Cy3, Cy5, or the like, generally available from the Amersham Biosciences division of GE Healthcare), the Alexa family of fluorescent dyes and other fluorescent and fluorogenic dyes available from Molecular Probes/Invitrogen, Inc., and described, e.g., in *The Handbook—A Guide to Fluorescent Probes and Labeling Technologies, Tenth Edition* (2005) (available from Invitrogen, Inc./Molecular Probes). A variety of fluorescent and fluorogenic labels for use with nucleobases, and which can be used for labeling nucleobases using available methods are described in, e.g., Published U.S. Patent Application No. 2003/0124576.

In labeling schemes utilizing FRET or similar phenomena, the enzyme can be labeled with the FRET dye member that is complementary to the FRET dye on the nucleotide. When the two dyes are brought into proximity, FRET occurs, resulting in a detectable signal. The dye on the enzyme can be attached through chemical modification, binding of an appropriate ligand or antibody that comprises the dye, or by incorporating an unnatural amino acid that comprises the dye into the enzyme. For example, systems of orthogonal elements can be used to site-specifically incorporate dye-containing unnatural amino acids, or to site-specifically incorporate reactive sites (e.g., keto or aldehyde groups) to which dyes can be chemically attached. For a review of orthogonal systems capable of incorporation of unnatural amino acids that comprise dyes or reactive groups, see, e.g., Wang et al. (2001), "Expanding the Genetic Code of *Escherichia coli*," *Science*, 292:498-500; Wang et al. (2002) "Expanding the Genetic Code," *Chem. Comm.* 1: 1-11; Wang and Schultz (2001) "A General Approach for the Generation of Orthogonal tRNAs," *Chemistry and Biology*, 8:883-890; Wang et al. (2003) "Addition of the Keto Functional Group to the Genetic Code of *Escherichia coli*," *Proc. Natl. Acad. Sci.* (*USA*), 100(1):56-61; Chin et al. (2003) "Progress Toward an Expanded Eukaryotic Genetic Code," *Chem. Biol.*, 10:511-519; Chin et al. (2003) "An Expanded Eukaryotic Genetic Code." *Science* 301:964-967; Deiters et al. (2003) "Adding Amino Acids with Novel Reactivity to the Genetic Code of *Saccharomyces Cerevisiae*." *J. Amer. Chem. Soc.*, 125(39):11782-11783; Wang and Schultz (2004) "Expanding the Genetic Code," *Angew. Chem.* 44(1):34-66; Xie and Schultz (2005) "Adding Amino Acids to the Genetic Repertoire," *Curr. Opin Chem Biol.* 9:548-554; Deiters and Schultz (2005) "In Vivo Incorporation of an Alkyne into Proteins in *Escherichia coli*." *Bioorg. Med. Chem. Lett.* 15(5):1521-4; and Xie and Schultz (2005) "An Expanding Genetic Code." *Methods*, 36(3):227-38.

Any of a variety of linkers can be used to link a label to a nucleotide (or polymerase). Other possible linkers including polyethylene glycol (PEG), double or single stranded DNA, alpha boronate, diaminoheptyl linkers, or the like. The lengths of the linkers can vary.

Finally, a variety of nucleotide labeling schemes, and enzymes (including polymerases) that are compatible with the resulting labeled nucleotides, are known. Polymerases or other enzymes used in these methods can be extrinsically or intrinsically modified as described above to provide exonucleases that sample the relevant labeled nucleotide, but that lack polymerization activity in the sequencing reaction mixture. For examples of nucleotide labeling approaches and complementary polymerases, See, e.g., Giller et al. (2003) "Incorporation of reporter molecule-labeled nucleotides by DNA polymerases. I. Chemical synthesis of various reporter group-labeled 2'-deoxyribonucleoside-5'-triphosphates" *Nucleic Acids Res.* 31(10): 2630-2635; Augustin et al. (2001) "Progress towards single-molecule sequencing: enzymatic synthesis of nucleotide-specifically labeled DNA" *J. Biotechnol.*, 86:289-301; Tonon et al. (2000) "Spectral karyotyping combined with locus-specific FISH simultaneously defines genes and chromosomes involved in chromosomal translocations" *Genes Chromosom. Cancer* 27:418-423; Zhu and Waggoner (1997) "Molecular mechanism controlling the incorporation of fluorescent nucleotides into DNA by PCR." *Cytometry*, 28:206-211. Yu et al. (1994) "Cyanine dye dUTP analogs for enzymatic labeling of DNA probes" *Nucleic Acids Res.*, 22:3226-3232; Zhu et al. (1994) "Directly labeled DNA probes using fluorescent nucleotides with different length linkers." *Nucleic Acids Res.* 22:3418-3422; Ried et al. (1992) "Simultaneous visualization of seven different DNA probes by in situ hybridization using combinatorial fluorescence and digital imaging microscopy" *Proc. Natl. Acad. Sci. USA*, 89:1388-1392.

Preparing Nucleic Acids for Sequencing

Nucleic acids to be sequenced can be obtained from any source of interest. These include isolation from a cell, cell culture, individual or synthetic source. Nucleic acids can be cloned, amplified, transcribed, ligated or otherwise manipulated according to standard methods to provide the nucleic acid to be sequenced.

Typically, the nucleic acid will be at least partially double stranded when sequencing is initiated. That is, the read position is determined by the terminal position of the complementary strand when hybridized to the template strand, and the exonuclease and nucleobase sampling activity proceeds along the complementary strand as it digests the complementary strand. To provide an at least partially double stranded nucleic acid, a double stranded nucleic acid (e.g., typically a double stranded DNA, though a double stranded RNA, or an RNA-DNA hybrid can also be used, depending, e.g., on the enzyme that is available for the sequencing reaction) can be provided from the source of interest, e.g., by isolating double stranded DNA. To provide termini that the exonuclease can digest, as well as a read/sampling site for nucleotide binding, the double stranded nucleic acid can be nicked using an appropriate nuclease (typically Deoxyribonuclease I (DNase I, generally known simply as "DNase")). The site of the nick serves as an initiation site for the sequencing reaction, in that it provides a terminus to the complementary strand that the exonuclease can initiate digestion from.

Another useful approach is to provide single stranded DNA templates, to which one or more primers are annealed. The primers can directly serve as initiation sites for the exonuclease, or the primer can be extended with a polymerase, prior to sequencing the template with the exonuclease.

While nucleic acids can be cloned and sequenced according to the present invention, in many cases cloning will not be necessary. In single-molecule sequencing applications, large preparations of nucleic acids are not needed to provide a nucleic acid of interest. Instead, genomic or other DNAs can be sequenced directly without an intermediate cloning step. Alternately, the nucleic acids can be amplified prior to cloning for one or more amplification cycles. Appropriate amplification methods can include PCR, linear PCR (linear rather than exponential amplification) transcription, or the like.

Procedures for isolating, cloning and amplifying nucleic acids are replete in the literature and can be used in the present invention to provide a nucleic acid to be sequenced. Further details regarding nucleic acid cloning, amplification and isolation can be found in Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2000 ("Sambrook"); *The Nucleic Acid Protocols Handbook* Ralph Rapley (ed) (2000) Cold Spring Harbor, Humana Press Inc (Rapley); *Current Protocols in Molecular Biology*, F. M. Ausubel et al., eds., Current Protocols, a joint venture between Greene Publishing Associates, Inc. and John Wiley & Sons, Inc., (supplemented through 2007) ("Ausubel")); *PCR Protocols A Guide to Methods and Applications* (Innis et al. eds) Academic Press Inc. San Diego, Calif. (1990) (Innis); Chen et al. (ed) *PCR Cloning Protocols, Second Edition* (Methods in Molecular Biology, volume 192) Humana Press; in Viljoen et al. (2005) *Molecular Diagnostic PCR Handbook* Springer; Demidov| and Broude (eds) (2005) *DNA Amplification: Current Technologies and Applications*. Horizon Bioscience, Wymondham, UK; and Bakht et al. (2005) "Ligation-mediated rolling-circle amplification-based approaches to single nucleotide polymorphism detection" *Expert Review of Molecular Diagnostics*, 5(1) 111-116. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A plethora of kits are commercially available for the purification of plasmids or other relevant nucleic acids from cells, (see, e.g., EasyPrep™, FlexiPrep™, both from Pharmacia Biotech; StrataClean™, from Stratagene; QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See Sambrook, Ausubel and Berger. In addition, essentially any nucleic acid can be custom or standard ordered from any of a variety of commercial sources, such as Operon Technologies Inc. (Huntsville, Ala.).

Systems for Detecting Transient Binding of the Nucleobase

In one aspect, the invention provides a sequencing system for practicing the methods herein. As an initial matter, the system includes a reaction chamber that the sequencing reaction is carried out in. In preferred embodiments, this reaction chamber is configured to perform single-molecule sequencing reactions, in which a single nucleic acid molecule of interest is sequenced in the chamber using the sampling/exonuclease digestion approach described herein.

In one example reaction of interest, a sequencing reaction can be isolated in the chamber within an extremely small observation volume that effectively results in observation of individual polymerase molecules. As a result, the sampling event provides observation of a sampled labeled nucleobase that is readily distinguishable from any signals produced from non-sampled nucleobases, e.g., that may be free in solution. In a preferred aspect, such small observation volumes are readily provided by immobilizing the polymerase enzyme within an optical confinement structure, such as a Zero Mode Waveguide. For a description of ZMWs and their application in single molecule analyses, and particularly nucleic acid sequencing, see, e.g., Published U.S. Patent Application No. 2003/0044781, and U.S. Pat. No. 6,917,726, each of which is incorporated herein by reference in its entirety for all purposes. See also, Levene et al. (2003) "Zero Mode Waveguides for single Molecule Analysis at High Concentrations," *Science* 299:682-686; U.S. Pat. Nos. 7,033,764, 7,052,847, 7,056,661 and 7,056,676. The individual reaction volumes on a ZMW can typically be on the order of, e.g., about 50 zeptoliters.

In many cases, ZMWs are provided in arrays of 10, 100, 1000, 10,000 or more waveguides. As such, immobilization of a single sequencing reagent, e.g., an enzyme and/or nucleic acid of interest, within each and every ZMW is unnecessary. Instead, dilution based protocols are used for delivering materials to the ZMWs, producing some ZMWs that are not occupied by an enzyme or other sequencing reagent (or both), but generally resulting in the majority of occupied ZMWs (those having at least one enzyme or nucleic acid molecule immobilized therein) having only one or the otherwise desired small number, of enzymes and nucleic acids located therein. In particular, in the case of ZMWs having exonucleases and nucleic acids located therein, typically, more than 50% of the occupied ZMWs have a single enzyme and nucleic acid located therein, preferably, greater than 75%, and more preferably greater than about 90% and even greater than 95% of the occupied ZMWs will have the desired number of sequencing reagent molecules, which in particularly preferred aspects will be one, but can be two, three or up to ten molecules of a given type. In some circumstances, different reagents may also be provided at a desired density to provide a mixed functionality sequencing surface, e.g., to test the activity of the exonuclease, or the condition of the nucleic acid to be sequenced.

The system includes a detector configured to detect a signal from the reaction chamber. As has been noted, the signal results from a transient template-dependent binding of a labeled nucleobase by an exonuclease in the reaction chamber. Detection is typically performed by exciting the observation volume with an appropriate light source, such as a laser, and then detecting induced fluorescence with appropriate detection optics. Often, the excitation and detection optics are integrated (e.g., using an epi-fluorescent excitation/detection apparatus).

Signals that are detected can be digitized and sent to a sequence assembly module that assembles the signals from sampling events into an overall sequence of the template nucleic acid. This assembly module will typically include system instructions, e.g., system software running on a CPU, e.g., a personal computer. Available sequencing software, which is already configured to convert digital signal information into sequence information can be adapted to generate sequences in the present invention. In general, appropriate system software operates by assembling nucleic acid sequences based upon detection of signals from the reaction chamber, wherein the signals are correlated to template nucleotides based upon the signal type and timing of the signals.

Figure 4:
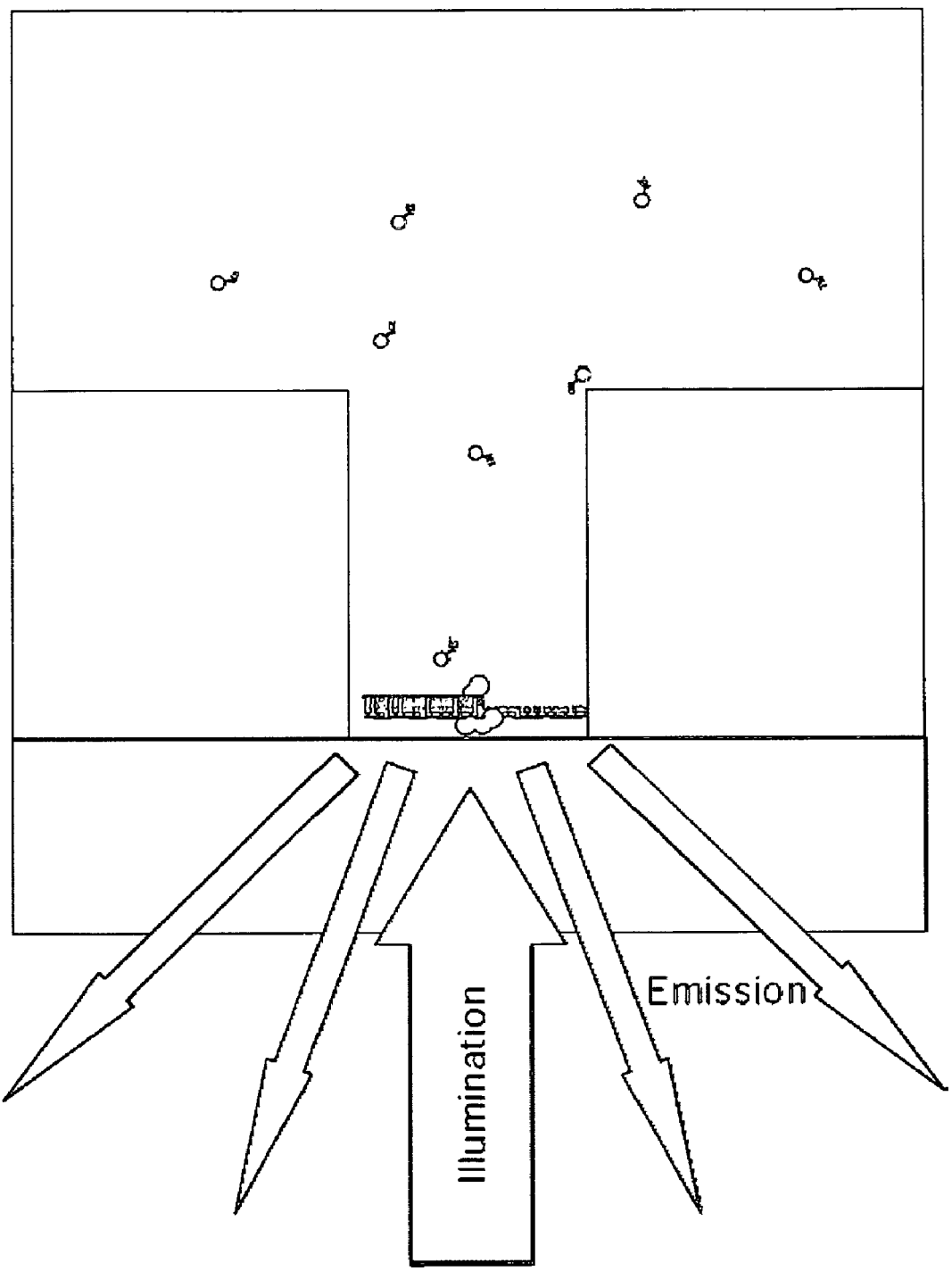
FIG. 4 provides a schematic illustration of a ZMW system in operation.

FIG. 4 provides a schematic illustration of a ZMW-based sequencing system, illustrating a ZMW, illumination source, path of emission photons, and an enzyme/template complex with labeled nucleobases.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method of sequencing at least a portion of a template nucleic acid, the method comprising:
   (a) providing a sequencing reaction mixture comprising:
      (i) the template nucleic acid;
      (ii) a complementary nucleic acid that is at least partially complementary to the template nucleic acid, wherein the complementary nucleic acid is hybridized to the template nucleic acid;
      (iii) an exonuclease that comprises template dependent nucleobase binding activity; and,
      (iv) at least one labeled nucleobase;
   (b) permitting the sequencing reaction mixture to react, such that the exonuclease transiently binds the labeled nucleobase in a template dependent manner, wherein the exonuclease moves along the template as it digests the complementary nucleic acid, wherein said nucleobase is not incorporated by said exonuclease; (c) detecting transient binding of the labeled nucleobase by the exonuclease; and, (d) determining a sequence of the template, or a portion thereof, based upon said detecting.

2. The method of claim 1, wherein the sequencing reaction mixture comprises magnesium as the primary cation in the reaction mixture.

3. The method of claim 1, wherein the template and complementary nucleic acids are produced by cutting one strand of a duplex DNA.

4. The method of claim 1, wherein the exonuclease is a DNA polymerase that, in the reaction mixture, is substantially free of nucleotide polymerization activity.

5. The method of claim 4, wherein the DNA polymerase is extrinsically modified to reduce inherent polymerization activity.

6. The method of claim 4, wherein the DNA polymerase is intrinsically modified to reduce inherent polymerization activity.

7. The method of claim 4, wherein the polymerase is a φ-29 polymerase that is deficient in polymerization activity in the reaction mixture, and that is exonuclease competent.

8. The method of claim 1, wherein the reaction mixture comprises a plurality of types of nucleobases, wherein different types of nucleobases comprise distinguishable fluorescent labels.

9. The method of claim 8, wherein the different types comprise four different labeled nucleobases, wherein each nucleobase is a nucleoside, nucleotide, deoxynucleoside or deoxynucleotide, or analog thereof, and wherein the labeled nucleobases each comprise an adenine, a guanine, a cytosine, a thymine or a uracil group, or an analog thereof, wherein each of the nucleobase types comprises a different distinguishable fluorescent label.

10. The method of claim 1, wherein the exonuclease transiently binds a first nucleobase at a first position on the template, digests a first nucleobase from the complementary strand, resulting in the exonuclease moving to a second position on the template where it transiently binds a second nucleobase in a template dependent manner, wherein each of the transient binding events are detected and wherein determining the sequence is based on detecting each transient binding event.

11. The method of claim 1, wherein (b) comprises:
   (i) transiently binding a first nucleobase by the exonuclease in an initial read position along the template;
   (ii) digesting a nucleobase from the complementary strand, moving the exonuclease to an additional read position along the template;
   (iii) transiently binding a second nucleobase with the exonuclease in the additional read position in a template dependent manner; and,
   (iv) repeating steps (ii)-(iii), with each step comprising digestion of the complementary strand to move the exonuclease into a new additional read position and transient template dependent binding of a nucleobase at the new read position, wherein the steps are repeated for (N) cycles, with (N) being selected by a user, or determined by the length of the complementary strand that can be digested by the exonuclease;
   wherein transient binding of the respective nucleobase at the initial and each additional read position is detected, thereby determining the sequence of the template at each read position along the template.

12. The method of claim 11, wherein (N) is between about 5 and about 50,000 nucleotides.

13. The method of claim 1, wherein (c) comprises detecting one or more optical signal generated by transient binding of the nucleobase by the exonuclease.

14. The method of claim 13, wherein the optical signal is a fluorescent signal produced by cleavage of a fluorophore from the nucleobase by the exonuclease.

15. The method of claim 13, wherein the optical signal is a fluorescent signal produced by proximity of a fluorophore of the nucleobase to a nucleobase binding site of the exonuclease, or to the template nucleic acid.

16. The method of claim 1, wherein (d) comprises assembling sequence information from a plurality of detectable signals produced by binding of a plurality of nucleobases by the exonuclease as the exonuclease travels along the template nucleic acid by digesting the complementary strand, wherein the signals correspond to a nucleobase type and position on the template nucleic acid.

17. The method of claim 16, wherein the sequence information is assembled from detection of a plurality of signals from a plurality of reactions collectively comprising overlapping template nucleic acids, wherein the signals in each of the respective reactions are produced by transiently binding a nucleobase to the exonuclease as the exonuclease travels along the template nucleic acid in each respective reaction by digesting the complementary strand in that reaction, wherein the signals correspond to a nucleobase type and position along the template nucleic acid in the respective reaction.

* * * * *